United States Patent [19]
Bahrmann

[11] Patent Number: 6,025,529
[45] Date of Patent: Feb. 15, 2000

[54] PROCESS FOR PREPARING ALDEHYDES

[75] Inventor: Helmut Bahrmann, Hamminkeln, Germany

[73] Assignee: Celanese GmbH, Germany

[21] Appl. No.: 09/211,936

[22] Filed: Dec. 15, 1998

[30] Foreign Application Priority Data

Dec. 22, 1997 [DE] Germany ............ 197 56 946

[51] Int. Cl.$^7$ .................... C07C 45/50
[52] U.S. Cl. ............ 568/454; 568/451; 502/208
[58] Field of Search ................. 568/451, 454; 502/208

[56] References Cited

U.S. PATENT DOCUMENTS

| | | | |
|---|---|---|---|
| 3,931,332 | 1/1976 | Wilkes | 260/604 HF |
| 3,976,703 | 8/1976 | Wilkes | 260/632 HF |
| 4,716,250 | 12/1987 | Abatjoglou et al. | 568/454 |
| 5,874,638 | 2/1999 | Chauvin et al. | 568/454 |

FOREIGN PATENT DOCUMENTS

| | | |
|---|---|---|
| 0216315 | 4/1987 | European Pat. Off. . |
| 0776880 | 6/1997 | European Pat. Off. . |
| 195 32 393 | 3/1997 | Germany . |

*Primary Examiner*—Shailendra Kumar
*Assistant Examiner*—Sreeni Padmanabhan
*Attorney, Agent, or Firm*—Bierman, Muserlian and Lucas

[57] ABSTRACT

A process for preparing aldehydes by hydroformylation of olefins or olefinically unsaturated compounds in the presence of a catalyst of at least one rhodium compound and a nonaqueous ionic ligand liquid of the formula $(Q^+)_a A^{a-}$, where $Q^+$ is a singly charged quaternary ammonium and/or phosphonium cation or the equivalent of a multiply charged ammonium and/or phosphonium cation and $A^{a-}$ is a sulfonated triarylphosphine.

15 Claims, No Drawings

PROCESS FOR PREPARING ALDEHYDES

A process for preparing aldehydes by hydroformylation of olefins or olefinically unsaturated compounds in the presence of at least one rhodium compound and in the presence of a nonaqueous ionic ligand liquid of the formula $(Q^+)_a\ A^{a-}$, where $Q^+$ is a singly charged quaternary ammonium and/or phosphonium cation or the equivalent of a multiply charged ammonium and/or phosphonium cation and $A^{a-}$ is a sulfonated triarylphosphine.

STATE OF THE ART

As valuable intermediate, aldehydes have great economic importance. From them, it is possible to prepare, for example, alcohols, carboxylic acids and amines which are in turn used as starting materials for producing important end products.

It is known that aldehydes can be prepared by reacting olefins with carbon monoxide and hydrogen which reaction is catalyzed by hydridometal carbonyls, preferably those of the metals of group VIII of the Periodical Table of the Elements. While cobalt was the first catalyst metal which was widely used industrially, processes for preparing aldehydes which use rhodium as catalyst metal have now become established in industry.

The preparation of aldehydes can be carried out in a single organic phase with the catalyst, e.g. a rhodium/triphenylphosphine complex, present as a solution in the organic reaction mixture. Furthermore, the preparation of aldehydes can also be carried out in the presence of an organic solvent such as toluene, xylene or tetrahydrofuran.

However, the separation of the reaction products and the recovery of the catalysts homogeneously dissolved in the reaction product present problems in this process. In general, the reaction product is distilled from the reaction mixture, but in practice, owing to the thermal sensitivity of the aldehydes formed, this method can only be used in the hydroformylation of lower olefins, i.e. olefins of up to about 5 carbon atoms in the molecule. In addition, thermal stressing of the material being distilled can lead to considerable losses of product as a result of by-product formation and to losses of catalyst as a result of decomposition of the catalytically active complexes.

These deficiencies can be avoided if the hydroformylation reaction is carried out in a two-phase system. Such a process is described, for example, in DE-C 26 27 354 which process is distinguished by the presence of an organic phase comprising the starting olefins and the reaction product and an aqueous phase in which the catalyst is dissolved. Catalysts used are water-soluble rhodium complexes which contain water-soluble phosphines as ligands. The phosphines include, particularly triarylphosphines, trialkylphosphines and arylated or alkylated diphosphines whose organic radicals are substituted by sulfonic acid groups or carboxyl groups. Their preparation is known, for example, from DE-C 26 27 354.

The hydroformylation process carried out in a two-phase system in the presence of an aqueous catalyst-containing phase is particularly useful in the hydroformylation of lower olefins, such as ethylene and propylene. If, however, higher olefins such as hexene, octene or decene are used, the conversion drops appreciably. The drop in the conversion is caused by the decrease in solubility of higher olefins in water, since it is assumed that the reaction between the reactants proceeds in the aqueous phase. The olefin conversion is significantly increased if a phase transfer reagent (solubilizer) is added to the aqueous catalyst solution. According to EP-B-O 562 451 solubilizers which have been found to be useful are, particularly cationic solubilizers of the formula $[A–N(R^1R^2R^3)]^+\ E^-$, where A is alkyl of 6 to 25 carbon atoms, $R^1$, $R^2$, $R^3$ are individually alkyl of 1 to 4 carbon atoms and $E^-$ is an anion, particularly sulfate, tetrafluoroborate, acetate, methosulfate, benzenesulfonate, alkylbenzenesulfonate, toluene-sulfonate, lactate or citrate.

Carrying out the hydroformylation process in a two-phase system in the presence of an aqueous catalyst containing phase requires not only sufficient solubility of the olefin in the aqueous phase but also sufficient stability of the olefin to be reacted toward water. For this reason, water-sensitive olefins such as acrylic esters or unsaturated acetals cannot be successfully used in this process.

To overcome this disadvantage without giving up the advantage of the two-phase hydroformylation process, the use of nonpolar perfluorinated hydrocarbons e.g. perfluoromethyl-cyclohexane, as a nonaqueous phase immiscible with the organic reaction product has been proposed for the catalytic hydroformylation of olefins. However, specific fluorinated ligands such as tris-(1H,1H, 2H-perfluorooctyl)phosphine are necessary to dissolve the rhodium, complexes in the perfluorinated hydrocarbons (Science, 1994, Vol 266, p. 72).

Another way of carrying out catalytic reactions in a nonaqueous two-phase system is described in CHEMTECH, September 1995, pages 26 to 30. According to this, non-aqueous ionic liquids which are liquid at room temperature, e.g. a mixture of 1,3-dialkylimidazolium chloride, preferably 1-n-butyl-3-methylimidazolium chloride, and aluminum chloride and/or ethylaluminum dichloride, can be used as nonaqueous solvents in which the catalyst complex is present in solution form. In the prior art, the 1-n-butyl-3-methylimidazolium cation is abbreviated as $BMI^+$.

An example of a reaction successfully carried out in this way is the dimerization of olefins in the presence of nickel complexes, e.g. the dimerization of propene to give isomeric hexenes or the dimerization of butene to give isooctenes. The reaction product forms the upper phase while the catalyst-containing nonaqueous ionic liquid forms the lower phase and can be separated off by simple phase separation. The catalyst-containing nonaqueous ionic liquid can be returned to the process.

It is known from Am. Chem. Soc., Div. Pet. Chem (1992), 37, pages 780 to 785, that a nonaqueous ionic liquid comprising 1-butyl-3-methylimidazolium chloride and aluminum chloride can serve as a solvent in which, after addition of ethylaluminum dichloride and $NiCl_2(PR_3)_2$ where R is isopropyl, the dimerization of propene is carried out.

The use of low-melting phosphonium salts, e.g. tetrabutylphosphonium bromide, as solvent in hydroformylation —reactions is disclosed in Journal of Molecular Catalysts, Vol. 47 (1988), pages 99–116. According to this, the hydroformylation of olefins, e.g. 1-octene, using ruthenium carbonyl complexes in the presence of nitrogen- or -phosphorus-containing ligands, e.g. 2,2'-bipyridyl or 1,2-bis(diphenyl-phosphino) ethane, at temperatures of from 120 to 180° C. gives a mixture of n-nonanol and n-nonanal. In this process, n-nonanol is obtained in a proportion of up to 69% by weight, based on the reaction mixture, so that a complicated distillation step is required to isolate the desired n-nonanal.

EP-A-0 776 880 discloses the hydroformylation of olefins in the presence of quaternary ammonium and/or phosphonium salts as solvent, with preference being given to using the 1-n-butyl-3-methylimidazolium cation

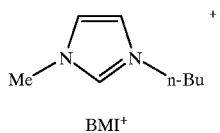

BMI⁺ as cation. However, use is also made of salts of quaternary diamines in which the cation has the formula

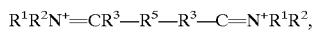

R¹R²N⁺=CR³—R⁵—R³—C=N⁺R¹R², where $R^1$, $R^2$, $R^3$ are individually hydrogen or hydrocarbon of 1 to 12 carbon atoms and $R^5$ is alkylene, e.g. methylene, ethylene or propylene, or phenylene. Suitable anions are, for example, hexafluorophosphate, hexafluoro-antimonate, tetrachloroaluminate and tetrafluoroborate. These quaternary ammonium and/or phosphonium salts are liquid at below 90° C., preferably below 85° C. and more preferably below 50° C. The hydroformylation catalyst is present as a solution in them.

The hydroformylation catalyst comprises cobalt, rhodium, iridium, ruthenium, palladium or platinum as active metal and a tertiary phosphine or tertiary sulfonated phosphine, a tertiary arsine, tertiary stibine or a phosphite as ligand. According to EP-A-0 776 880, the molar ratio of ligand to metal is 9.5. Examples of suitable compounds which contain the active metals and from which the hydroformylation catalyst is formed under the reaction conditions are dicarbonyl-rhodium acetylacetonate and rhodium, carbonyl $Rh_6(CO)_{16}$ Particular preference is given to carrying out the hydroformylation reaction at from 30 to 90° C.

Angew. Chem. 1995, Vol. 107, No. 23/24, pages 2941 to 2943, also discloses the use of 1,3-dialkylimidazolium salts which are liquid at room temperature as catalyst-containing solvent which is immiscible with the organic reaction mixture for carrying out hydroformylation reactions. Here, dicarbonylrhodium acetylacetonate is added as catalyst precursor to a solution of triphenyl-phosphine in BMI⁺ hexafluorophosphate, with the molar ratio of phosphorus (III) to rhodium varying from 3 to 10. The catalyst is preformed by addition of synthesis gas containing hydrogen and carbon monoxide in a volume ratio of 1:1. After addition of 1-n-pentene, the reaction is carried out using synthesis gas of the same composition at a temperature of 80° C. In this case too, the organic product phase can be separated from the catalyst-containing nonaqueous ionic liquid in a simple manner by decantation.

The known processes for the hydroformylation of olefins all use a nonaqueous ionic liquid as solvent for the catalytically active metal complexes. The use of the nonaqueous ionic liquids as solvents introduces additional anions which do not serve as ligands, e.g. hexafluoroantimonate or hexafluorophosphate, into the hydroformylation process.

Furthermore, the prior art known from Angew. Chem. 1995, Vol 107, No. 23/24, pages 2941 to 2943, and EP-A-0-776 880 teaches a molar ratio of phosphorus to rhodium of from 3 to 10. Higher molar ratios of phosphorus to rhodium are not disclosed in the prior art. A higher molar ratio of phosphorus to rhodium presumably leads to precipitation or an increased loss of the phosphine ligand from the nonaqueous ionic liquid disclosed.

A disadvantage of the known processes is, apart from the loss of the phosphine ligand, the loss of the catalytically active metal from the nonaqueous ionic liquid to the organic phase. According to the prior art, this disadvantage can be overcome by using charged ligands, e.g. monosulfonated or trisulfonated triphenylphosphine, in place of neutral ligands, e.g. triphenylphosphine, since it is to be expected that charged ligands will increase the solubility of the catalytically active metal compounds in the nonaqueous ionic liquid. Even if it were possible to reduce the loss of the catalytically active metals by use of charged ligands, the yields of aldehydes are decreased to only 16–33% (Angew. Chem. 1995, Vol. 107, No. 23/24, pages 2941 to 2943, EP-A-0 776 880).

OBJECTS OF THE INVENTION

It is an object of the invention to develop a process which uses a nonaqueous ionic ligand liquid and, after addition of a catalytically active metal and/or its compound, gives the desired aldehydes in a simple way and in high yields. This and other objects and advantages of the invention will become obvious from the following detailed description.

THE INVENTION

The invention provides a process for preparing aldehydes by reacting monoolefins, non-conjugated polyolefins, cycloolefins or derivatives of this class of compounds with carbon monoxide and hydrogen at temperatures of from 20 to 150° C. and pressures of from 0.1 to 20 MPa in the presence of a nonaqueous ionic ligand liquid of the formula $(Q^+)_a A^{a-}$ and at least one rhodium compound, wherein $Q^+$ is a singly charged quaternary ammonium and/or phosphonium cation or the equivalent of a multiply charged ammonium and/or phosphonium cation and $A^{a-}$ is a triarylphosphine of the formula

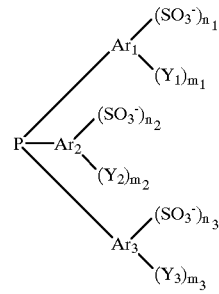

where $Ar_1$, $Ar_2$, and $Ar_3$ are individually of 6 to 14 carbon atoms, $Y_1$, $Y_2$ and $Y_3$ are individually selected from the group consisting of alkyl and alkoxy of 1 to 4 carbon atoms, chlorine, bromine, hydroxyl, cyano, nitro and —$NR^1R^2$, where $R^1$ and $R^2$ are individually hydrogen, or alkyl of 1 to 4 carbon atoms, $m_1$, $m_2$ and $m_3$ are individually integers from 0 to 5, $n_1$, $n_2$ and $n_3$ are individually integers from 0 to 3, where at least one of $n_1$, $n_2$ and $n_3$ is equal to or greater than 1, and a is $n_1+n_2+n_3$, and amines and/or phosphines derived from $Q^+$ are present in an excess of up to 5 equivalents over the stoichiometrically required amounts for the formation of $(Q^+)_a A^{a-}$ or alkali metal and/or alkaline earth metal salts of the triarylphosphine $A^{a-}$ are present in an excess of up to 5 equivalents over the stoichiometrically required amount for the formation of $(Q^+)_a A^{a-}$.

It has surprisingly been found that the nonaqueous ionic ligand liquids of the invention are, after addition of rhodium and/or its compounds, very useful as catalyst system for the hydroformylation of olefins or olefinically unsaturated compounds. It has been found that the use of the nonaqueous ionic ligand liquids in hydroformylation processes allows the use of a high molar ratio of phosphorus to rhodium of up to 1000 to 1.

A high excess of ligand, e.g. of sulfonated triphenylphosphine, has a stabilizing effect on the catalytically active metal complexes during the catalysis cycle.

In the following, "catalyst system" means the nonaqueous ionic ligand liquid together with the catalytically active rhodium, compounds. Stabilized catalyst systems have a low rate of loss of rhodium and allow frequent recycling of the used catalyst system to the hydroformylation process without a drop in catalyst activity and selectivity being observed. Stabilized catalyst systems therefore give higher yields of aldehydes and have longer catalyst operating lives than unstabilized catalyst systems.

When using nonaqueous ionic liquids and nonaqueous ionic ligand liquids, the lengthening of the catalyst operating lives, as is known to be able to be achieved by means of stabilized catalyst systems, is of particular importance since the exhausted catalyst phase after discharge from the hydroformylation process represents a substantial salt burden which has to be dealt with by costly reprocessing and/or disposal. Exhaustion of the catalyst system is indicated by a drop in the catalyst activity and selectivity to a level below that which is economically acceptable.

The decreases in activity and selectivity are caused, for example, by the accumulation of catalyst degradation products. If two-phase processes catalyzed by transition metals are carried out in nonaqueous ionic liquids, excessively rapid exhaustion of the catalyst system which requires the subsequent discharge from the hydroformylation process is therefore a particular disadvantage. The nonaqueous ionic ligand liquids of the invention make it possible to employ a molar ratio of phosphorus to rhodium of up to 1000 to 1 which is known to increase the stability and thus the life of phosphine-substituted catalysts.

It may be assumed that the catalytically active rhodium compounds are formed from the rhodium, which is added either in metallic form or as customary rhodium compounds, and the nonaqueous ionic ligand liquid in the presence of carbon monoxide and hydrogen. The nonaqueous ionic ligand liquid and the catalytically active rhodium compound form the catalyst system.

The use of the nonaqueous ionic ligand liquids of the invention in hydroformylation reactions makes it possible to dispense with the addition of additional anions which do not serve as ligands in such processes. The nonaqueous ionic ligand liquids of the invention can comprise amines and/or phosphines derived from $Q^+$ in an excess over the stoichiometrically required amount for formation $(Q^+)_a A^{a-}$ or alkali metal and/or alkaline earth metal salts of the triarylphosphine $A^{a-}$ in an excess over the stoichiometrically required amount for formation of $Q^+_a A^{a-}$. In general, the excess over the stoichiometrically required amount for formation of $(Q^+)_a A^{a-}$ is up to 5 equivalents of amines and/or phosphines derived from $Q^+$ or of alkali metal and/or alkaline earth metal salts of the triaryl-phosphine $A^{a-}$ and this excess is preferably from 0 to 1 equivalent.

Cations $Q^+$ which can be used for preparing the nonaqueous ionic ligand liquids of the invention are quaternary ammonium and/or phosphonium cations of the formula $^+NR^1R^2R^3R^4$ or $^+PR^1R^2R^3R^4$ or the formula $R^1R^2N^+=CR^3R^4$ or $R^1R^2P^+=CR^3R^4$, where $R^1$, $R^2$, $R^3$ and $R^4$ are individually hydrogen, with the exception of $NH_4^+$, or hydrocarbon of 1 to 20 carbon atoms, for example alkyl, alkenyl, cycloalkyl, alkylaryl, aryl or aralkyl.

Other cations suitable for preparing the nonaqueous ionic ligand liquids of the invention are heterocyclic ammonium and/or phosphonium cations of the formulae

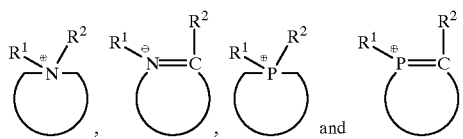

which have 1, 2 or 3 nitrogen and/or phosphorus atoms in the ring,. The heterocycles have from 4 to 10, preferably 5 or 6, ring atoms. $R^1$ and $R^2$ are as defined above.

Further suitable cations are quaternary ammonium and -phosphonium cations of the formulae

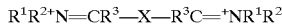

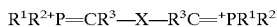

where $R^1$, $R^2$ and $R^3$ are individually as defined above and X is alkylene or phenylene. $R^1$, $R^2$, $R^3$ may be, for example, methyl, ethyl, propyl, isopropyl, butyl, secondary butyl, tertiary butyl, amyl, methylene, ethylidene, phenyl or benzyl. X is 1,2-phenylene, 1,3-phenylene, 1,4-phenylene or alkylene, for example methylene, ethylene, propylene or 1,4-butylene.

Other cations $Q^+$ which are suitable for preparing the nonaqueous ionic ligand liquid of the invention are N-butylpyridinium, N-ethylpyridinium 1-n-butyl-3-methylimidazolium, diethylpyrazolium, 1-ethyl 3-methylimidazolium, pyridinium, triethylphenyl ammonium and tetrabutylphosphonium cations.

Further cations $Q^+$ which are suitable for preparing the nonaqueous ionic ligand liquids of the invention are quaternary ammonium and/or phosphonium cations of the formulae

 (quaternary diamines)

 (quaternary diphosphines)

where $R^1$, $R^2$, $R^3$, $R^4$, $R^5$ and $R^6$ are individually hydrogen of 1 to 20 carbon atoms, for example alkyl, alkenyl, cycloalkyl, alkylaryl, aryl or aralkyl, and X is 1,2-phenylene, 1,3-phenylene, 1,4-phenylene- or $(CHR^7)_b$, where $R^7$ is hydrogen or hydrocarbon of 1 to 5 carbon atoms, for example methyl, ethyl, n-propyl, i-propyl, n-butyl, i-butyl or t-butyl, and b is an integer from 1 to 8. Examples of X are methylene, ethylene, propylene, butylene and 1,4-phenylene.

The quaternary ammonium cations of the formula $R^1R^2R^3N^+$ (X) $N^+R^4R^5R^6$ are hereinafter referred to as quaternary diamines.

Quaternary diamines which are suitable for preparing the nonaqueous ionic ligand liquids of the invention include those quaternary diamines of the formula $R^1R^2R^3N^+$ $(CHR^7)_b$ $N^+R^4R^5R^6$ in which $R^1$, $R^2$, $R^3$, $R^4$, $R^5$ and $R^6$ are individually hydrogen, n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl or i-dodecyl, $R^7$ is hydrogen, methyl or ethyl and b is 2, 3, 4, 5 or 6.

Quaternary diamines which are particularly suitable for preparing the nonaqueous ionic ligand liquids of the invention are those which are derived from 1-amino-3-dialkylaminopropanes of the formula

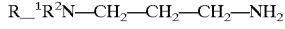

where $R^1$ and $R^2$ are individually alkyl of 4 to 20 carbon atoms, for example n-butyl, n-pentyl, n-hexyl, n-heptyl, i-heptyl, n-octyl, i-octyl, i-nonyl, n-nonyl, n-decyl, i-decyl, n-undecyl, i-undecyl, n-dodecyl or i-dodecyl.

The nonaqueous ionic ligand liquids of the invention can be prepared particularly advantageously if 1-amino-3-(di-n-heptyl)aminopropane, 1-amino-3-(di-i-heptyl) aminopropane, 1-amino-3-(di-n-octyl)aminopropane, 1-amino-3-(di-i-octyl)aminopropane, 1-amino-3-(di-n-nonyl)aminopropane, 1-amino-3-(di-i-nonyl) aminopropane, 1-amino-3-(di-n-undecyl)aminopropane, 1-amino-3-(di-i-undecyl)amin opropane, 1-amino-3-(di-n-dodecyl)amino-propane or 1-amino-3-(di-i-dodecyl)-aminopropane is used for preparing the quaternary diamines.

The 1-amino-3-dialkylaminopropanes are prepared by reacting N,N-(dialkyl)amines of the formula $R^1R^2NH$ where $R^1$ and $R^2$ are individually alkyl of 4 to 20 carbon atoms, particularly n-butyl, n-pentyl, n-hexyl, n-heptyl, i-heptyl, n-octyl, i-octyl, i-nonyl, n-nonyl, n-decyl, i-decyl, n-undecyl, i-undecyl, n-dodecyl or i-dodecyl, with acrylonitrile by known methods (cf. Ullmanns Encyclopedia of Industrial Chemistry Vol. A2, 1985).

As further diamines derived from $Q^+$, it is possible to use tricyclodecanediamine and N,N'-dimethyltricyclo-decane diamine.

The triarylphosphines $A^{a-}$ used for carrying out the process of the invention can be obtained from the alkali metal and/or alkaline earth metal salts of the triarylphosphines of the formula

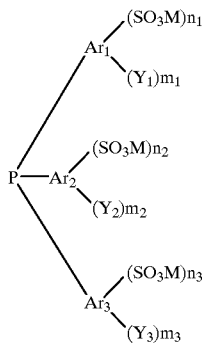

in which $Ar_1$, $Ar_2$ and $Ar_3$ are individually aryl of 6 to 14 carbon atoms, $Y_1$, $Y_2$ and $Y_3$ are individually alkyl or alkoxy of 1 to 4 carbon atoms, chlorine, bromine, hydroxyl, cyano, nitro or $R^1$ and $R^2$ are individually hydrogen or alkyl of 1 to 4 carbon atoms, M is lithium, sodium, potassium, magnesium, calcium or barium, $m_1$, $m_2$ and $m_3$ are individually integers from 0 to 5, $n_1$, $n_2$ and $n_3$ are individually integers from 0 to 3, where at least one of $n_1$, $n_2$ and $n_3$ is equal to or greater than 1, which are known from DE-A-26 27 354.

Preferred triarylphosphines are those in which $Ar_1$, $Ar_2$, $Ar_3$ are phenyl, $Y_1$, $Y_2$ and $Y_3$ are methyl, ethyl, methoxy or ethoxy and/or a chlorine atom, and the cationic radicals M are inorganic cations of sodium, potassium, calcium or barium. Particularly suitable triarylphosphines are those in which $Ar_1$, $Ar_2$, $Ar_3$ are phenyl, $m_1$, $m_2$, $m_3$ are 0, $n_1$, $n_2$ and $n_3$ are 0 or 1 and the sum of $n_1+n_2+n_3$ is from 1 to 3 and in which the sulfonated groups are in the meta position.

Aqueous solutions of sodium, potassium, calcium or barium salts of (sulfophenyl)diphenylphosphine, di(sulfophenyl)phenylphosphine or tri(sulfophenyl)-phosphine are particularly suitable. It is also possible to use mixtures of these aqueous solutions. However, it is advantageous to use a single aqueous salt solution of one of the above-mentioned alkali metals and/or alkaline earth metals, particularly an aqueous sodium or potassium salt solution. This solution may also contain a mixture of (sulfophenyl)-diphenylphosphine, di(sulfophenyl)phenylphosphine and tri (sulfophenyl)phosphine.

A mixture suitable for carrying out the hydroformylation process of the invention is obtained in the sulfonation of triphenylphosphine, as known, for example, from DE-A 26 27 354.

If tricyclodecanediamine or N,N'-dimethyltricyclodecanediamine is used as amine for preparing the nonaqueous ionic ligand liquid, a mixture having as high as possible a content of di(sulfophenyl)-phenylphosphine should be used.

The process for preparing the nonaqueous ionic ligand liquid is the subject matter of a patent application filed on the same day herewith (docket RUH-258).

The process of the invention can be used to react monoolefins, non-conjugated polyolefins, cyclic olefins and derivatives of these unsaturated compounds. The olefins can be straight-chain or branched and the double bonds can be terminal or internal. Examples of olefins which can be used in the novel process are ethylene, propylene, 1-butene, 2-butene, 1-pentene, 2-methyl-l-butene, 1-hexene, 2-hexene, 1-heptene, 1-octene, 3-octene, 3-ethyl-l-hexene, 1-decene, 3-undecene, 4,4-dimethyl-1-nonene, dicyclopentadiene, vinylcyclohexene, cyclooctadiene and styrene. Derivatives of the types of olefins mentioned which can be hydroformylated by the method are, for example, alcohols, aldehydes, carboxylic acids, esters, nitrites and halogen compounds, allyl alcohol, acrolein, methacrolein, crotonaldehyde, methyl acrylate, ethyl crotonate, diethyl fumarate and diethyl maleate and acrylonitrile.

The process of the invention allows the hydroformylation of, particularly water-sensitive olefins and olefin derivatives, e.g. vinyl acetate, vinyl propionate, vinyl butyrate, allyl acetate, allyl propionate, allyl butyrate, acrylates of 4 to 20 carbon atoms, acrolein dialkyl acetals having alkyl of 1 to 17 carbon atoms and other olefin derivatives which have a hydrolysis-sensitive group, e.g. an ester or amide group, in the molecule, in good yields. The process is used particularly successfully for hydroformylating olefins and olefin derivatives of 2 to 20 carbon atoms.

The reaction mixture comprising the olefin used and the aldehyde which has already been formed can be used as organic phase, with or without addition of solvent. If a solvent is added, preference is given to using toluene, o-xylene, m-xylene, p-xylene, mesitylene, benzene, cyclohexane, tetrahydrofuran, n-hexane, n-heptane or n-octane.

Rhodium is used either as metal or as a compound. In metallic form, it is used either as finely divided particles or deposited in a thin layer on a support such as activated carbon, calcium carbonate, aluminum silicate or alumina. Suitable rhodium compounds are salts of aliphatic mono-carboxylic and polycarboxylic acids, e.g. rhodium 2-ethylhexanoate, rhodium acetate, rhodium oxalate, rhodium propionate or rhodium malonate. It is also possible to use rhodium salts of inorganic hydrogen and oxo acids, e.g. rhodium nitrate or rhodium sulfate, the various rhodium oxides or else rhodium carbonyl compounds such as $Rh_3(CO)_{12}$ or $Rh_6(CO)_{16}$ or complexes of rhodium, e.g. cyclooctadienyl-rhodium compounds or rhodium acetyl acetonate. Rhodium-halogen compounds are less suitable because of the corrosive behavior of the halide ions. Preference is given to rhodium oxide and, particularly rhodium acetate and rhodium 2-ethyl-hexanoate.

The catalyst system can first be formed in a preforming step and then added as a preformed catalyst system to the reaction mixture. In this case, the desired amount of rhodium, preferably as rhodium 2-ethylhexanoate solution, is added to the nonaqueous ionic ligand liquid and the reaction mixture is treated at a temperature of 100 to 120° C. with a synthesis gas at a pressure of 0.5 to 5 MPa for a time of up to 5 hours. After preformation of the catalyst, the reaction of the olefins with hydrogen and carbon monoxide is carried out at temperatures of from 20 to 150° C., preferably from 80 to 140° C. and more preferably, from 100 to 125° C., and pressures of from 0.1 to 20 MPa, preferably from 1 to 12 MPa and more preferably from 3 to 7 MPa.

The preforming step can also be carried out in the presence of a solvent, e.g. in the presence of toluene, o-xylene, m-xylene, p-xylene, cyclohexane or heptane. Preference is given to using toluene or cyclohexane as solvent.

The composition of the synthesis gas, i.e. the ratio of carbon monoxide to hydrogen, can be varied within wide limits. In general, use is made of synthesis gas in which the volume ratio of carbon monoxide to hydrogen is 1:1 or differs only slightly from this value.

The catalyst system can be prepared equally successfully under the reaction conditions, i.e. in the presence of the olefin. Here, the olefin and aldehyde can serve as solvent for the catalyst. If an additional solvent is employed, preference is given to using toluene, o-xylene, m-xylene, p-xylene, cyclohexane, mesitylene or n-heptane, particularly toluene or cyclohexane.

The rhodium concentration is from 2 to 1000 ppm by weight, preferably from 3 to 400 ppm by weight and more preferably from 5 to 100 ppm by weight, based on the amount of olefin used.

The sulfonated triarylphosphines $A^{a-}$, which are a constituent of the nonaqueous ionic ligand liquid of the invention, are present in an excess based on the amount of rhodium used.

The ratio of rhodium to the sulfonated triarylphosphine $A^{a-}$, also expressed as the ratio of rhodium to phosphorus (III) can be varied within wide limits. Generally, from 2 to 1000 mol of phosphorus (III) can be employed per mole of rhodium and preference is given to a molar ratio of phosphorus(III) to rhodium of from 3 to 300 and preferably from 20 to 100.

The reaction can be carried out either batchwise or continuously. After the reaction is complete, an organic aldehyde-containing upper phase is obtained and the catalyst system is present as a lower phase and these two phases can be separated from one another by simple phase separation. After phase separation, the catalyst system can be returned to the hydroformylation process.

In the following examples, there are described several preferred embodiments to illustrate the invention. However, it is to be understood that the invention is not intended to be limited to the specific embodiment.

EXAMPLE 1

Hydroformylation of n-hexene in the presence of 1-amino-3-(di-i-nonyl)aminopropane/trisulfophenyl-phosphine.

Use was made of a nonaqueous ionic ligand liquid comprising 1-amino-3-(di-i-nonyl)aminopropane and tri (sulfophenyl)phosphine as described in the patent application Serial No. 212,822 filed Dec. 16, 1998, which is hereby incorporated by reference. An excess of 0.45 equivalent of the sodium salts of the triarylphosphine was present in the nonaqueous ionic ligand liquid used.

420 g of the nonaqueous ionic ligand liquid were placed in a 1 liter autoclave and admixed with a rhodium 2-ethylhexanoate solution in 2-ethylhexanol in an amount corresponding to a molar ratio of phosphorus (III) to rhodium of 136 to 1. Then, n-hexene was added in such an amount that the rhodium concentration, based on the amount of olefin used, was 400 ppm by weight. The reaction with synthesis gas was carried out at a temperature of 125° C. and a pressure of 4 MPa for 1.5 hours. The reaction was then stopped, the autoclave was vented and the organic phase (the reaction product) was removed via an immerse tube and analyzed. The olefin conversion was 71%, and the ratio of n-heptanal to 2-methylhexanal was 69:31. The catalyst system was recirculated twice without conversion and selectivity deteriorating.

EXAMPLE 2

Hydroformylation of n-hexene in the presence of 1-amino-3-(di-n-octyl)aminopropane/trisulfophenyl-phosphine.

Use was made of a nonaqueous ionic ligand liquid comprising 1-amino-3-(di-n-octyl)aminopropane and tri (sulfophenyl)phosphine as described in the patent application filed on the same day herewith, which is hereby incorporated by reference. An excess of 1.1 equivalents of 1-amino-3-(di-n-octyl)aminopropane was present in the nonaqueous ionic ligand liquid used.

In a 1 liter autoclave, 485 g of the nonaqueous ionic ligand liquid were admixed with 306 g of cyclohexane and then admixed with a solution of rhodium 2-ethylhexanoate in 2-ethylhexanol in an amount corresponding to a molar ratio of phosphorus(III) to rhodium of 64 to 1. n-Hexene was subsequently added in such an amount that the rhodium concentration, based on the amount of olefin used, was 400 ppm by weight. The reaction with synthesis gas was carried out at a temperature of 125° C. and a pressure of 2.5 MPa for a time of 45 minutes. The reaction was then stopped, the autoclave was vented and the reaction product was removed via an immersed ube and analyzed. The olefin conversion was 97%, and the ratio of n-heptanal to 2-methylhexanal was 66:34.

EXAMPLE 3

Hydroformylation of n-hexene in the presence of 1-amino-3-(di-n-octyl)aminopropane/trisulfophenyl-phosphine; recirculation tests.

The catalyst system employed in Example 2 was repeatedly used for the hydroformylation of n-hexene under the same hydroformylation conditions as in Example 2. As can be seen from Table 1, a high yield of the aldehydes was observed, even after multiple recirculation of the catalyst system. It was surprisingly found that when using the nonaqueous ionic ligand liquids of the invention, the loss rates of rhodium (amount of rhodium found in 1 kg of organic reaction product) decreased steadily on multiple recirculation.

TABLE 1

| | Recirculation test for the hydroformylation of n-hexene using the catalyst phase employed in Example 2 | | | | | | | | | | | | | | | |
|---|---|---|---|---|---|---|---|---|---|---|---|---|---|---|---|---|
| Re-use | 1 | 2 | 3 | 4 | 5 | 6 | 7 | 8 | 9 | 10 | 11 | 12 | 13 | 14 | 15 | 16 |
| Olefin addition (g) | 100 | 100 | 100 | 100 | 100 | 100 | 100 | 100 | 100 | 100 | 130 | 100 | 100 | 100 | 100 | 100 |
| Cyclohexane addition (g) | 110 | 130 | 130 | 130 | 130 | 130 | 130 | 130 | 130 | 390 | 390 | 130 | 130 | 130 | 390 | 390 |
| Conversion (%) | 95.6 | 92.2 | 94 | 94.3 | 85 | 78.8 | 52.6 | 95.1 | 95.5 | 94.4 | 93.3 | 93.4 | 91.1 | 92.8 | 92.5 | 90.5 |
| Ratio of n-heptanal 2-methylhexanal | 65/35 | 65/35 | 66/34 | 66/34 | 66/34 | 69/31 | 75/25 | 69/31 | 69/31 | 64/36 | 69/31 | 70/30 | 67/33 | 69/31 | 69/31 | 69/31 |
| Rhodium loss (mg/kg) | 8.01 | 2.77 | 4.2 | 3.09 | 1.51 | 0.88 | 0.02 | 1.56 | 1.51 | 0.76 | 0.80 | 0.46 | 0.82 | 0.84 | 0.3 | 0.36 |

Various modifications of the catalyst and process for the invention may be made without departing from the spirit or scope thereof and it should be understood that the invention is intended to be limited only as defined in the appended claims.

What I claim is:

1. A process for preparing aldehydes comprising reacting a member selected from the group consisting of monoolefins, non-conjugated polyolefins, cycloolefins and derivatives of this class of compounds with carbon monoxide and hydrogen at temperatures of 20 to 150° C. and pressures of 0.1 to 20 MPa in the presence of a nonaqueous ionic ligand liquid of the formula $(Q^+)_3 A^{a-}$ and at least one rhodium compound, wherein $Q^+$ is a singly charged quaternary ammonium and/or phosphonium cation or the equivalent of a multiply charged ammonium and/or phosphonium cation and $A^{a-}$ is a triarylphosphine of the formula

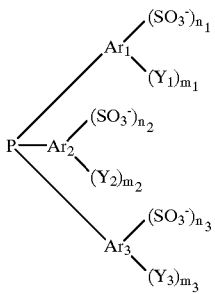

where $Ar^1$, $Ar^2$ and $Ar^3$ are individually aryl of 6 to 14 carbon atoms, $Y_1$, $Y_2$ and $Y_3$ are individually selected from the group consisting of alkyl of 1 to 4 carbon atoms, alkoxy of 1 to 4 carbon atoms, chlorine, bromine, hydroxyl, cyano, nitro and —$NR^1R^2$, where $R^1$ and $R^2$ are individually hydrogen or of 1 to 4 carbon atoms, $m_1$, $m_2$ and $m_3$ are individually integers from 0 to 5, $n_1$, $n_2$ and $n_3$ are individually integers from 0 to 3, where at least one of $n_1$, $n_2$ and $n_3$ is equal to or greater than 1, and a is $n_1+n_2+n_3$, and amines and/or phosphines derived from $Q^+$ are present in an excess of up to 5 equivalents over the stoichiometrically required amounts for the formation of $(Q^+)_a A^{a-}$ or alkali metal and/or alkaline earth metal salts of the triarylphosphine $A^{a-}$ are present in an excess of up to 5 equivalents over the stoichiometrically required amount for the formation of $(Q^+)_a A^{a-}$.

2. The process of claim 1, wherein amines and/or phosphines derived from $(Q^+)$ are present in an excess of up to 1 equivalent over the stoichiometrically required amount for the formation of $(Q^+)_a A^{a-}$ or alkali metal or alkaline earth metal salts of the triarylphosphine $A^{a-}$ are present in an excess of up to 1 equivalent over the stoichiometrically required amount for the formation of $(Q^+)_a A^{a-}$.

3. The process of claim 1, wherein $Q^+$ is a member of the group consisting of $^+NR^1R^2R^3R^4$, $^+PR^1R^2R^3R^4$, $R^1R^2N^+=CR^3R^4$, $R^1R^2P^+=CR^3R^4$, or

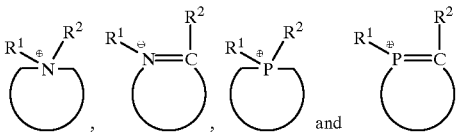

where $R^1$, $R^2$, $R^3$ and $R^1$ are individually hydrogen, with the exception of $NH_4^+$, or hydrocarbon of 1 to 20 carbon atoms and in which the heterocycles have from 4 to 10 ring atoms.

4. The process of claim 1 wherein $Q^+$ is a quaternary ammonium and/or phosphonium cation selected from the group consisting of $R^1R^{2+}N=CR^3$—X—$R^3C=^+NR^1R^2$ and $R^1R^{2+}P=CR^3$—X—$R^3C=^+PR^1R^2$, where $R^1$, $R^2$ and $R^3$ are individually hydrogen and hydrocarbon of 1 to 20 carbon atoms and X is alkylene or phenylene.

5. The process of claim 1, wherein $Q^+$ is selected from the group consisting of N-butylpyridinium, N-ethylpyridinium, 1-n-butyl-3-methylimidazolium, diethylpyrazolium, 1-ethyl-3-methyl imidazolium, pyridinium, triethylphenylammonium, and tetrabutylphosphonium cation.

6. The process of claim 1, wherein $Q^+$ is a quaternary ammonium and/or phosphonium cation of the formula $R^1R^2R^3N^+$ (X) $N^+R^4R^5R^6$ or $R^1R^2R^3P^+$ (X) $P^+R^4R^5R^6$,

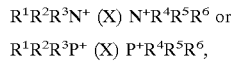

where $R^1$, $R^2$ $R^3$, $R^4$, $R^5$ and $R^6$ are individually hydrogen or hydrocarbon of 1 to 20 carbon atoms and X is selected from the group consisting of 1,2-phenylene, 1,3-phenylene, 1,4-phenylene and $(CHR^7)_b$, where $R^7$ is hydrogen or hydrocarbon of 1 to 5 carbon atoms and b is an integer from 1 to 8.

7. The process of claim 6, wherein $R^1$, $R^2$, $R^3$, $R^4$, $R^5$ and $R^6$ are individually selected from the group consisting of hydrogen, n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl and i-dodecyl, $R^7$ is hydrogen, methyl or ethyl and b is 2, 3, 4, 5 or 6.

8. The process of claim 7, wherein $R^1$ and $R^2$ are individually selected from the group consisting of n-butyl, n-pentyl, n-hexyl, n-heptyl, i-heptyl, n-octyl, i-octyl, n-nonyl, i-nonyl, n-decyl, i-decyl, n-undecyl, i-undecyl, n-dodecyl and i-dodecyl, $R^3$, $R^4$, $R^6$ are hydrogen, $R^7$ is hydrogen and b is 3.

9. The process of claim 1, wherein $Q^+$ is the tricyclodecanediammonium cation or the N,N'-dimethyltricyclodecanediammonium cation.

10. The process of claim 1, wherein from 2 to 1000 mol, of phosphorus(III) are used per mole of rhodium.

11. The process of claim 1, wherein the rhodium concentration is from 2 to 1000 ppm by weight, based on the amount of olefin used.

12. The process of claim 1, wherein the reaction is carried out at from 20 to 150° C.

13. The process of claim 1, wherein the reaction is carried out at pressures of from 0.1 to 20 MPa.

14. The process of claim 1, wherein olefins or olefin derivatives of 2 to 37 carbon atoms are used.

15. The process of claim 1, wherein the organic aldehyde-containing phase and the rhodium-containing nonaqueous ionic ligand liquid are separated from one another by phase separation and the rhodium-containing nonaqueous ionic ligand liquid separated off is returned completely or partially to the hydroformylation reactor.

\* \* \* \* \*